US 6,894,434 B1
May 17, 2005

(12) United States Patent
Kosoff

(54) NIGHTLIGHT AND LAMP CONTROL

(76) Inventor: Richard S. Kosoff, 6211 Jared Ct., Woodland Hills, CA (US) 91367

( * ) Notice: Subject to any disclaimer, the term of this patent is extended or adjusted under 35 U.S.C. 154(b) by 0 days.

(21) Appl. No.: 10/618,801

(22) Filed: Jul. 14, 2003

(51) Int. Cl.$^7$ ................................................. H01J 1/60
(52) U.S. Cl. ....................... 315/134; 362/227; 362/801; 315/360
(58) Field of Search ................................. 315/134, 149, 315/291, 307, 360; 362/1, 276, 362, 801, 20, 97, 227

(56) References Cited

U.S. PATENT DOCUMENTS

| 2,907,901 | A | | 10/1959 | Parker ......................... 307/112 |
| 4,000,405 | A | | 12/1976 | Horwinski ..................... 362/95 |
| 4,038,561 | A | | 7/1977 | Lorenz ......................... 307/141 |
| 4,497,582 | A | * | 2/1985 | Lipman et al. ................ 368/15 |
| 4,712,019 | A | | 12/1987 | Nilssen ........................ 307/141 |
| 5,307,051 | A | | 4/1994 | Sedlmayr .................. 340/573.1 |
| 5,319,283 | A | | 6/1994 | Elwell ......................... 315/194 |
| 5,430,598 | A | | 7/1995 | Rodolfo ....................... 361/115 |
| 5,646,594 | A | | 7/1997 | Barben et al. ............... 340/567 |
| D386,255 | S | | 11/1997 | Ying-teng ................... D23/364 |
| 6,242,872 | B1 | | 6/2001 | Ha ............................... 315/293 |
| 6,367,949 | B1 | * | 4/2002 | Pederson .................... 362/240 |
| D460,202 | S | | 7/2002 | Stekelenburg ............... D26/26 |
| 2002/0131262 | A1 | | 9/2002 | Amburgey .................... 362/95 |
| 2002/0149328 | A1 | | 10/2002 | Davies ........................ 315/291 |
| 2003/0057879 | A1 | | 3/2003 | Capriglione ................. 315/291 |
| 2003/0214259 | A9 | * | 11/2003 | Dowling et al. ............. 315/312 |

FOREIGN PATENT DOCUMENTS

WO    WO 85/00264    1/1985

* cited by examiner

Primary Examiner—Thuy Vinh Tran
(74) Attorney, Agent, or Firm—Colin P. Abrahams

(57) ABSTRACT

A nightlight and control unit comprises a nightlight housing including an illumination member and a control unit associated with the nightlight housing for regulating light in a light device connectable to the control unit. An input mechanism is provided for programming the control unit.

33 Claims, 3 Drawing Sheets

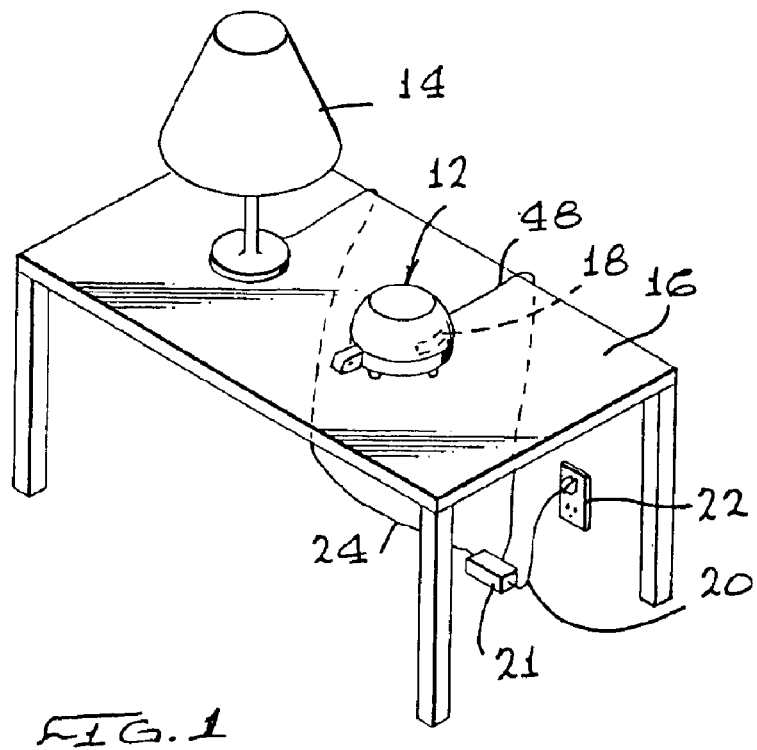
FIG. 1
FIG. 2
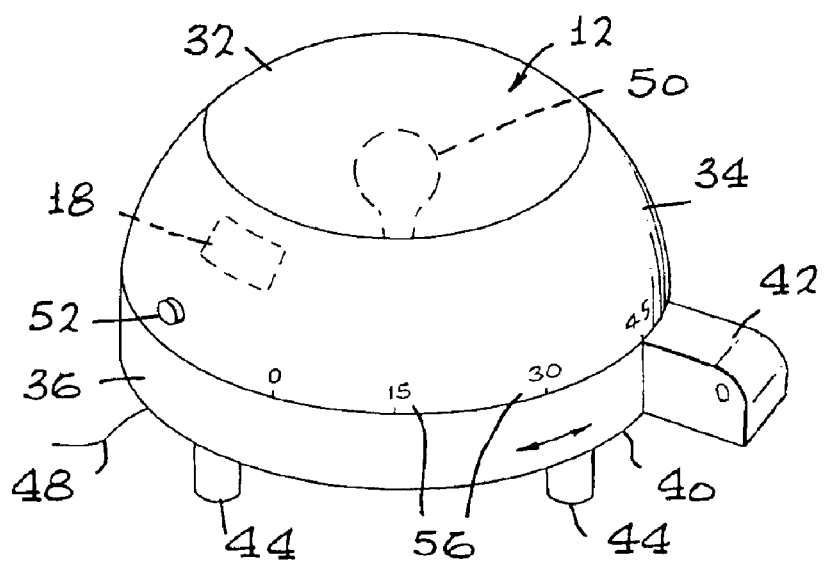

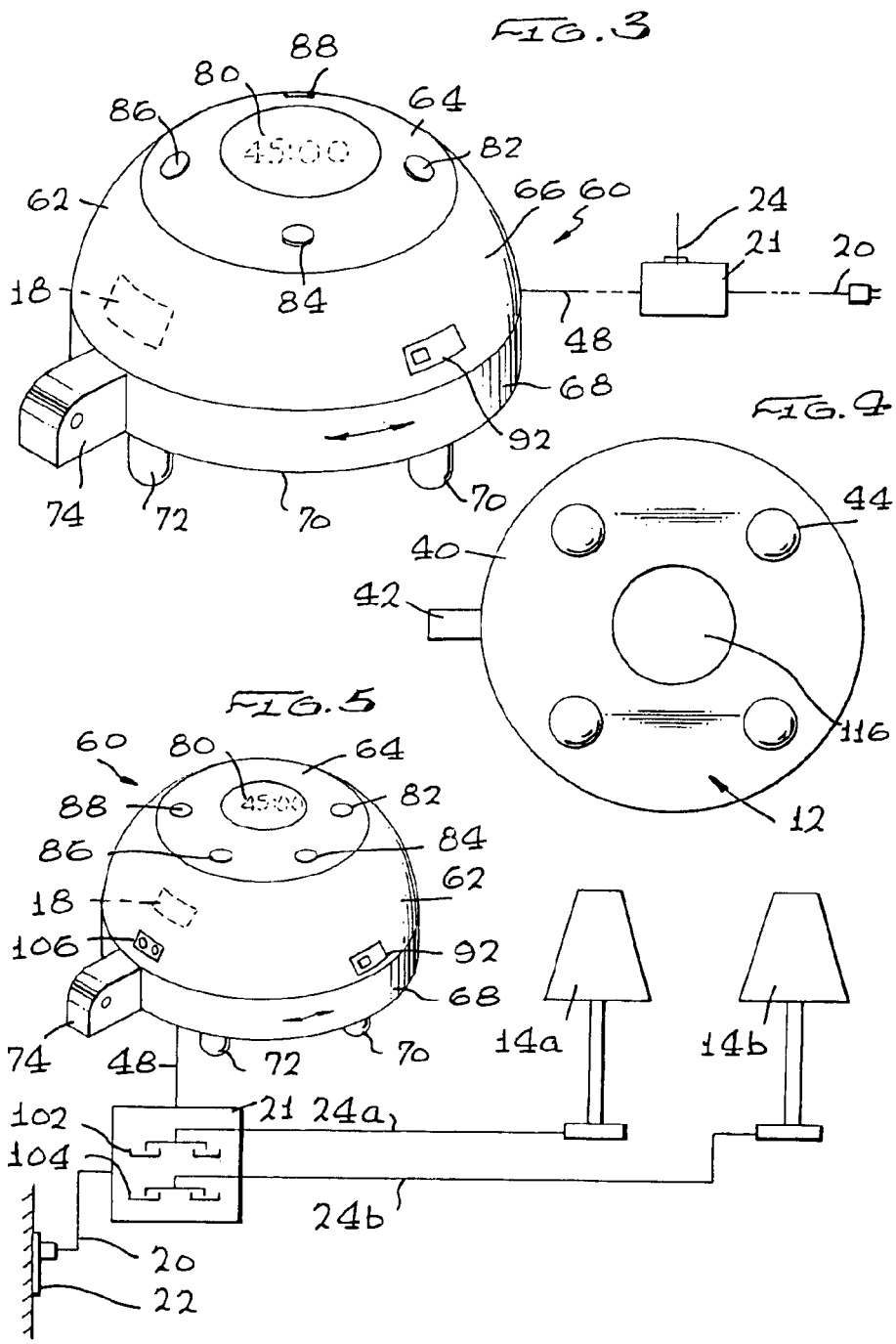

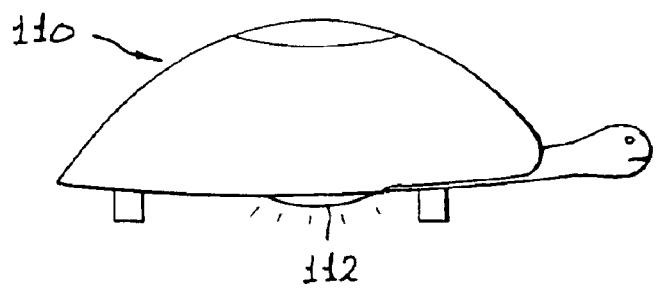
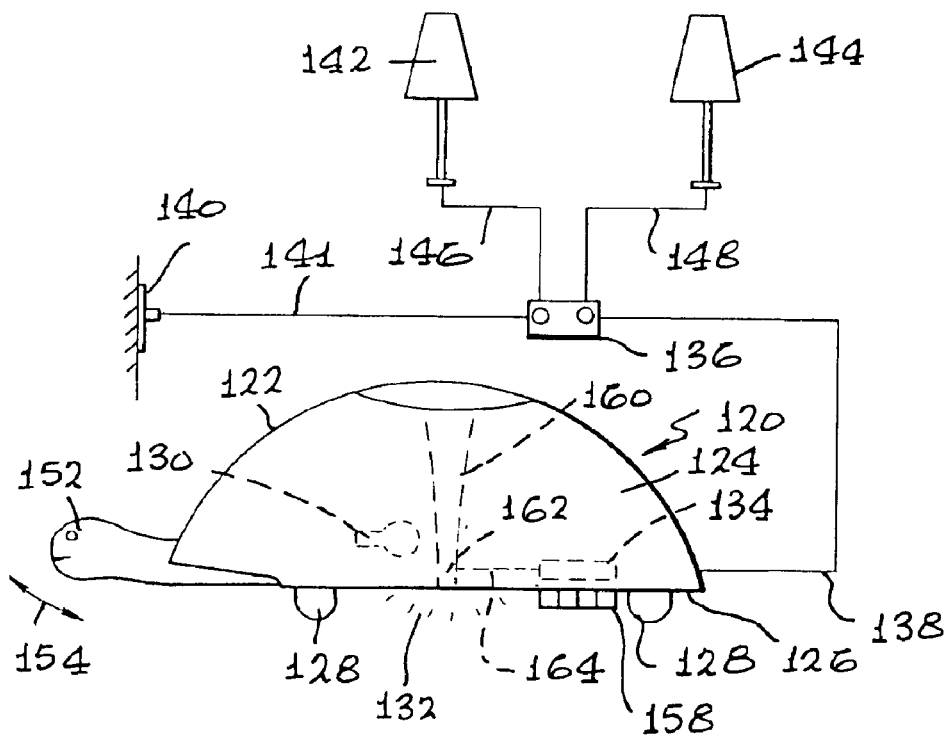

NIGHTLIGHT AND LAMP CONTROL

FIELD AND BACKGROUND OF THE INVENTION

This invention relates to a nightlight and lamp control. Specifically, the invention, in one aspect, is for a stand alone nightlight which is capable of controlling an associated light or lamp. The nightlight may provide a source of constant illumination, and is capable of controlling an associated lamp or light fitting so as to fade out the light given off by the lamp or light fitting over a preselected or predetermined period of time.

The invention has particular application with respect to use in children's bedrooms. In this regard, the nightlight and lamp of the invention can provide a low level light over the entire night in the child's bedroom, but at the same time slowly fade out an associated lamp or light over a given period of time. The associated lamp will be activated to commence the fade-out phase typically when a child is put to sleep, and the time of fade-out can be selected, for example, so as to coincide with at least the length of time it is known that the child takes to fall asleep.

Nightlights are, of course, well known and widely used in a number of contexts and applications. For example, in a child's bedroom, wall plug inserts or stand-alone light units, whether powered by AC or DC sources, are known. Some of these may be able to detect ambient light conditions, so that they are activated when ambient light falls below a predetermined level. Other nightlights can simply be switched on and off at will, and may, for example, be switched on at the time the child is going to sleep.

Various devices are also known by means of which the light provided by a lamp or light fixture can be slowly faded out or increased over a period of time. Some of these may, also, sense ambient light conditions, and slowly phase in to light up a room or area as light fades during sunset and the onset of night. Conversely, other types of light fittings may have the circuitry for programming them to fade-out over a given period of time, which may be in response to increasing ambient light levels at daybreak.

U.S. Pat. No. 5,646,594 (Barben) describes a lighting apparatus characterized by the use of motion detectors for controlling a lighting system. The motion detectors may also be utilized to activate other devices, such as radios, alarms, and the like, upon the approach of people. A dimmer control and timer assembly are incorporated into the circuit, all of which respond to the motion detector.

U.S. Pat. No. 2,907,901 (Parker) describes a sleep-inducing apparatus for sequentially dimming the brilliance of a light and then disconnecting it after a preselected time period. U.S. Pat. No. 4,712,019 (Nilssen) includes a self-contained programmable plug-in timer, while U.S. Pat. No. 4,038,561 (Lorenz) describes a circuit for a children's lamp including a timer mechanism which may automatically and gradually diminish the light level. U.S. Pat. No. 4,000,405 (Horwinski) describes an electrical adaptor and nightlight which provides multiple electric sockets and subdued illumination, and a switch which enables lamps to be selectively energized.

U.S. Patent Application No. US 2003/0057879 (Capriglione) teaches a lighting electronic controller which can switch on an external device such as a house lamp at a predetermined time, and automatically increase or decrease the level of intensity in gradual stages.

U.S. Patent Application No. US2002/0131262 (Amburgey) describes a nightlight and socket assembly including a light sensor which can replace a switch to provide automatic on and off for the night light.

SUMMARY OF THE INVENTION

As will be noted from the above, nightlights of various forms and characteristics are available, as are mechanisms and circuitry for increasing and decreasing the light intensity of a light unit, either over a predetermined time period or in response to some external condition, such as ambient light changes.

The invention provides both a nightlight, which consistently gives off a preferably variable intensity light, until switched off, the nightlight also controlling an associated lamp which can be dimmed over a period of time. The present invention therefore addresses the issue of not only providing a consistent low-level nightlight to, for example, small children, but also the ability for that nightlight to operate as a control mechanism for dimming out an associated light unit. In many instances, children, and especially young children, are uncomfortable when a room is substantially darkened over a very short period of time, such as by turning off a light, even when a nightlight may exist. The ability of the light to be faded over a period of time while the child goes to sleep may be more comforting to the child, and also may help the child to fall asleep more quickly. While the child is going to sleep, the room is not dark, although the light from the associated lamp will be fading in accordance with the present invention. Once the light from the associated lamp has been switched off, the nightlight itself will continue to give off a small amount of light so that, if the child should awaken during the night, the room will not be in darkness. At this time, of course, the child's eyes may have accommodated to the darker conditions, so that the presence of the low level nightlight alone will be comforting for the child.

In accordance with one aspect of the invention, there is therefore provided a nightlight, which is connectable to an associated lamp or light unit, wherein the nightlight gives off a consistent light over a period of time, such as during the night, while the associated lamp is dimmed from a fully or partially lighted condition to an off condition, over a period of time, which may be selected by the user.

In one form, the nightlight itself may be adjustable so that its light intensity can be varied, but, for most purposes, once set, will remain at the selected light intensity until switched off either manually or automatically. The automatic switch-off may occur as a result of a timing device, or by operation of an ambient light detector which will switch off the nightlight when the ambient light conditions in the room have reached a desired level.

According to one aspect of the invention, there is provided a nightlight and control unit comprising: a nightlight housing including an illumination member; a control unit associated with the nightlight housing for regulating light in a light device connectable to the control unit; and input means for programming the control unit.

The control unit may be located within the housing, or it may be outside of the housing and electrically connected thereto. The control unit may comprise a box, circuit board or other structure inside or outside the housing for containing circuitry for regulating light in the light device, a light device connector means for electrically connecting the light device with the control unit, a nightlight connecting means for connecting the control unit with the nightlight, and a power cable for connecting the nightlight to a power source.

The input means is preferably located on the nightlight housing and may comprise time-setting means, whereby the control unit is programmed to regulate the light device so that the light therefrom fades to off over a preselected time period.

The nightlight and control unit may further comprise a timer display for indicating time remaining for regulating the light in the light device. Adjustment means for adjusting the intensity of the illumination member may be provided.

The nightlight itself may preferably be shaped in the form of a turtle, other animal or other shape to appeal to a child. The nightlight may, for example, comprise a substantially hemispherical cover portion on a flat base. The light provided by the nightlight may be a low glow over the area, or a part of the area, of the hemispherical cover or dome, or the light may shine through the base. The nightlight may include an adjustment means for setting the intensity of the light provided thereby.

In one embodiment, the nightlight is connected to a control box or member, which may be integral therewith, or comprised as a separate unit placed away from the nightlight. The control box or member itself may have an electrical connector means so as to plug into a source of power, such as a wall plug outlet. Further, the control box will have connector means whereby an associated lamp can be plugged into it. The associated lamp so connected to the control box will receive both the necessary power from the control box, and the control box or member will have the circuitry and signal mechanisms for fading-out, or increasing, the light intensity of the associated lamp in accordance with the preset conditions selected by the user. Preferably, however, all control functions reside in the turtle or other shaped housing, and the lamp attachment will, for aesthetic reasons, have its attachment closer to the wall.

The control box may also have outlets for a plurality of lamps, which can be placed away from each other or at different points in the room, and the circuitry may permit each of the plurality of lamps to be timed and programmed to fade-out simultaneously with each other, or fade-out at different rates, so that different areas of the room may remain lighter, or become darker, more quickly than other areas of the room.

BRIEF DESCRIPTION OF THE DRAWINGS

FIG. 1 is a schematic perspective view of the nightlight and lamp control in accordance with the present invention;

FIG. 2 is a side perspective view of the nightlight in accordance with the present invention;

FIG. 3 is a top perspective view of the nightlight and control unit in accordance with the present invention;

FIG. 4 is a bottom view of the nightlight of the present invention;

FIG. 5 is a schematic representation showing the components and operation of the nightlight and control circuit, in conjunction with associated lamps, in accordance with the present invention;

FIG. 6 is a side perspective view of another embodiment of the nightlight of the invention showing a different shape and form of the device; and FIG. 7 is a side perspective view of another embodiment of the nightlight of the invention showing a further different shape and form of the device.

DETAILED DESCRIPTION OF THE INVENTION

Reference is now made to the accompanying drawings which show various forms, views and embodiments of the nightlight and lamp control in accordance with the present invention. The nightlight and control provides a continuous low-level light in the form of a night lamp, but also has circuitry and components associated therewith whereby an associated lamp or lamps can be connected thereto, and whose light intensity can be diminished or increased over a predetermined period of time, as may be selected by the user. The "start" intensity of the associated lamp can preferably be adjusted.

Reference is made to FIG. 1 of the drawings which shows a general schematic perspective view of the nightlight and lamp control in accordance with the present invention. The components of this nightlight and lamp control system include a nightlight unit 12, and an associated lamp 14. Both the nightlight unit 12 and associated lamp 14 will typically be placed on a flat surface 16 which in many circumstances will be a small table or night stand adjacent or near the child's bed. While the present invention has as one of its important applications the control of light within a child's room, it should be appreciated that the invention is not limited to such applications. For example, the nightlight unit and lamp control of the invention may be used as a security type mechanism, whereby lighting is switched on and off, and dimmed over time, in a house where the occupants may be away, to give the external appearance that the house is inhabited. Further, the unit is not limited to use in a child's bedroom, but can be used in any living room area or adult's bedroom, or even in commercial, retail or industrial settings where it is desired to have a consistent, low-level night light, but to fade-out, or fade-in, the light of an associated light unit.

The nightlight unit 12 includes a control unit 18. In the embodiment shown in FIG. 1 of the drawings, the control unit 18 is shown within the nightlight unit 12. The control unit 18 connects to a connector box 21 which is located external to the nightlight unit 12. However, in other forms of the invention, the control unit 18 may be separate and apart from the nightlight unit 12. One advantage of separating the connector box 21 from the nightlight unit 12, especially in a child's bedroom, would be to avoid unnecessary wiring or cables on the surface 16. Thus, the nightlight unit 12 and associated lamp 14 can be located on the surface 16, and their wires led directly under the surface 16 where the necessary electrical connections would be made. This may assist in placing the potentially hazardous electrical connections out of reach, and possibly out of sight, of the child, thus contributing to the additional safety of the nightlight and lamp control of the invention.

The connector box 21 has a power connector cable 20, which plugs into a conventional wall socket 22. As will become apparent below, the power connector cable 20 thus provides the necessary power source for the nightlight unit 12, the associated lamp 14, as well as any circuitry and other control devices which may be located within the control unit 18 or connector box 21 and the nightlight unit 12.

The associated lamp 14 has a conventional power cord 24, which plugs into the connector box 21. In this way, the control unit 18 and connector box 21 together are able to provide not only a power source for illuminating the associated lamp 14, but also the necessary controls for increasing, but usually decreasing, the intensity of the associated lamp 14 over a period of time, as will be described.

With reference to FIG. 2 of the drawings, there is shown a more detailed view of the nightlight unit 12. The nightlight unit 12 comprises a generally hemispherical dome cover 30 having a top portion 32 and a side portion 34. A rotatable annular slide switch 36 is formed below the side portion 34, and is mounted on the base 40 of the nightlight unit 12. The slide switch 36 includes a radially, outwardly projecting lever 42 for rotating the slide switch 36. The base 40 is mounted on four legs 44 which raises the base 40 so that it is somewhat spaced from the surface 16 on which the nightlight unit 12 may be located.

The nightlight unit 12 is connected to a connector box 21, not shown in FIG. 2, but which is discussed in further detail with reference to some of the other Figures. However, the nightlight unit 12 has a power and signal connector(s) 48 which connects to the connector box 21. The power and signal connector(s) 48 serves as a transmitter of power between the connector box 21 and the nightlight unit 12 to serve as a power source for the light within the nightlight unit 12. Further, the power and signal connector(s) 48 also serves as a medium by which programmed or selected features, such as timing, dimming periods, and other features selected on the nightlight unit 12 may be transmitted to the connector box 21, so that the connector box 21 in turn may operate the associated lamp 14 in accordance with the selections of the user.

The hemispherical dome cover 30, including the top portion 32 and side portion 34 may, in certain embodiments, be comprised of semi-opaque but translucent material so that illumination provided by a light bulb or light emitting diode (LED) 50 formed within the chamber defined by the dome cover 30 is emitted through the dome cover 30 to provide it with a comforting glow and a low level of light. However, in other embodiments, the dome cover 30 may be substantially opaque so that no light can escape therefrom, but a translucent window, as will be described, formed in the base 40 of the nightlight unit 12, may permit the light from the bulb or LED 50 to provide a low-level light. These are just two such embodiments, and the invention is not limited according to the nature by which light may be transmitted from inside of the nightlight unit 12 to the exterior thereof. Any type of window, whether located on the base 40 or dome cover 30 of the nightlight unit 12, or whether formed by translucent portions of the dome cover 30 or base 40, may fall within the scope of the invention whereby the low-level night light is provided.

The intensity given off by the light bulb or LED 50 in FIG. 2 of the drawings may be varied. Thus, some children or people may prefer the nightlight unit 12 to give off a fairly significant amount of light during the course of the night. However, other users may prefer that the intensity of the nightlight be much lower. To this end, an adjustment knob 52 may be provided in the dome cover 30 for modulating the intensity of the LED or light bulb 50, and thereby control the amount of light given off by the nightlight unit 12.

The nightlight unit 12 incorporates a mechanism whereby a user may select the amount of time it takes for the nightlight unit 12 to fade-out the associated lamp 14. In the embodiment shown in FIG. 2, this is provided in the form of a slide switch 36, which is easily operated by manipulating the lever 42. As will be seen, the dome cover 30 has printed thereon periods of time 56, and these are, in the embodiment of FIG. 2, provided in quarter-hour increments, and shown as 15 minutes, 30 minutes, 45 minutes and 60 minutes. Any desired interval may, however, be provided, and the invention is not limited to fading-out the associated lamp in an hour or less. Thus, the length of time for fading out the associated lamp may exceed an hour by any desired portion. A period of time 56 may be selected in the embodiment shown in FIG. 2 by rotating the slide switch 36 by grasping the lever 42. If the lever 42 is located in front of the "60"

period of time 56, indicating a 60 minute fade-out time, this is the time that it will take for the control unit 18 to fade-out the illumination of the associated lamp 14. The other periods of time 56 may also be selected, and, in one embodiment, the lever 42 may be placed anywhere along the scale between 0 and 60 to select the desired time.

In use, it will be seen that the nightlight unit 12 shown in FIG. 2 of the drawings thus has a variable intensity light bulb or LED 50 which gives off light over the entire period that the nightlight unit 12 is powered. This is substantially consistent, and will not change over a period of time. In addition, the slide switch 36 can be moved around and set so that the nightlight unit also provides signals to the connector box 21, as to how long the associated lamp 14 should remain illuminated, which represents the time that it will be faded out. Preferably, the control unit 18 will fade-out the associated lamp 14 incrementally so that a consistent fade-out to will be provided until the associated lamp 14 is switched off.

Reference is now made to FIG. 3 of the drawings, which shows another embodiment of the nightlight unit, designated with the reference numeral 60 in this figure, in accordance with the present invention. In this embodiment, the nightlight unit 60 is formed by a hemispherical dome cover 62 having a top portion 64 and side portion 66. A slide switch 68 is formed adjacent a base 70 of the nightlight unit 60, and legs 72 are provided, in much the same way as was shown and described with respect to FIG. 2 of the drawings.

As an example of the variations possible within the scope of the present invention, the slide switch 68 shown in FIG. 3 may be used by turning it with the lever 74 so as to vary the intensity of a light bulb, not shown, located within the chamber defined by the dome cover 62. As an alternative, it may be used to vary the intensity of the associated lamp 14. Further, a different method of setting the time of fade-out of the associated lamp is provided. At the top 64 of the dome portion 62, there is formed an LED or LCD display 80, and more or less equispaced around the display 80 are four time setting buttons 82, 84, 86 and 88. Each button represents a specific fade-out time. Thus, for example, button 82 may set the timer at 15 minutes for fading out the associated lamp; button 84 may set the timer at 30 minutes for fading out the associated lamp; button 86 may set the timer for 45 minutes (the time shown in the LCD display 80) for fading out the associated lamp; while button 88 may set the timer for 60 minutes for fading out the associated lamp. These are arbitrary times only, set in quarter hour increments, and any convenient, desirable time limits may be set. The fade out of the associated lamp 14 may start from full light intensity thereof or from a predimmed setting as determined by manually dimming thereof, such as by adjusting the position of the lever 74.

Extending from the nightlight unit 60 is a power and signal connector 48, having the same properties and characteristics as that described with reference to FIG. 2. The power and signal connector 48 connects to the connector box 21, and the connector box 21 is itself connected to a power source by means of the power connector cable 20. Also connected to the connector box 21 is a power cord 24, which supplies power and signals relating to diminishing intensity of light to the associated lamp 14.

With reference to FIG. 3, the nightlight unit 60 is set by first adjusting the lever 74 so that the desired brightness of the bulb within the dome cover 62 is obtained. Thereafter, one of the four time setting buttons 82, 84, 86 and 88 is set, and selected based on the preferred time limit for fading out the associated lamp 14. Once set in motion, the LCD display 80 will begin to count backward, towards zero, indicating the amount of time left until such time as the associated lamp 14 will be disconnected from power, and will be switched off.

The nightlight and control unit of the invention may in addition have an on-off button 92 for switching the entire unit on or off. Further, the outlet of the connector box 21 may have input for two or more associated lamps, so that each lamp can be controlled, either as a group, or with individual fade-out times for each lamp. In FIG. 3, the on-off switch 92 is shown for activating and deactivating the entire mechanism.

FIG. 4 shows a bottom view of the nightlight unit 12 shown in FIG. 2 of the drawings. The base 40 is shown, including the legs 44, and a window 116 is shown which is transparent or translucent so that a light bulb illuminated within the nightlight unit 12 can pass therethrough. The light will therefore shine, for example, on the surface 16, but gently spread so as to provide a low-level intensity nightlight within the room in which it is used.

Reference is now made to FIG. 5 of the drawings which is a schematic representation showing a total system of the invention. In FIG. 5, there is shown a nightlight unit 60 having most of the features and characteristics of that shown in FIG. 3 of the drawings. Thus, the nightlight unit 60 includes the LCD display, the dome cover 62, the slide switch 68 operated by the lever 74, all mounted on a base 70 which is supported on legs 72. The buttons 82 to 88 are formed on the top of the dome cover 66 for easy access and setting by the user. Further, the switch 92 is provided for the entire system.

Extending from under the base 70 of the nightlight unit 60, the power and signal connector 48 extends to the connector box 21. The connector box 21 has the power connector cable 20, which plugs into a conventional wall socket 22. In the embodiment shown in FIG. 5, the connector box 21 has two associated lamp outlets 102 and 104. A power cord 24a extends from the outlet 102 to lamp 14a. Separately, a power cord 24b extends from the power outlet 104 to supply the lamp 14b. Where the connector box 21 permits more than one lamp to be connected thereto, the nightlight unit 60 may, for example, include a selector switch 106 so that each of the lamps 14a and 14b can be separately programmed for fade-out time.

In use, and in one particular embodiment of the invention, the connector box 21 will be separate from the nightlight unit 60. However, it is within the scope of the invention to place the connector box 21 within the chamber defined by the dome portion 62, with the associated lamp outlets 102 and 104 either being located on the outside of the dome portion 62, or having a separate connector away from the nightlight unit 60, and preferably close to the wall socket.

In another variation of the invention, the control unit 18 may be regulated remotely. Thus, a remote control unit, not shown, held by the user may be capable of transmitting a signal to a receiver, which may be located within the nightlight unit 60 or within the connector box 21. By appropriately pressing selected buttons on the remote control unit, the fade-out time of the associated lamp can be set, and, in some embodiments, the intensity of the nightlight which will consistently shine can also be varied.

The control unit 18 will include the necessary circuitry for effecting the fade-out or fade-in times of the associated lamp 14, based on the settings selected on the nightlight unit. The invention is not limited to any one form of circuit board or circuitry, but any components which are able to effect the necessary fade-out time based on the settings in the nightlight unit can be used.

FIG. 6 shows yet a further embodiment of the invention, but will have the essential features and characteristics of the nightlight described with reference to the previous drawings. In FIG. 6 there is shown a nightlight unit 110 wherein the dome-shaped portion is in the shape of a turtle body, and the lever 74 is in the shape of a turtle head. The legs are in the shape of a turtle's legs, and an LED display area 80 is provided on the top thereof. On the base or underside of the dome there is provided a lens 112 through which light from a bulb, not shown, formed within the body of the dome, can pass, thus providing the necessary illumination.

With reference to FIG. 7 of the drawings, there is shown a nightlight unit 120 having a housing 122 comprising a dome shaped cover 124 and a base 126. The housing 122 is shaped like a turtle and includes ornamental legs 128. A bulb or LED 130 is located in the housing 122 and the light given off thereby, indicated by reference numeral 132, emanates through a translucent window or area in the base 128. The cover 124 and entire base 126 may also be translucent so that the whole or a part of the housing 122 glows, as may be desired.

The housing 122 accommodates a control unit 134 which is electrically connected to connector box 136 by means of a connector cable 138. The connector box 136 itself is connected to a power source 140, which is typically a wall socket outlet, by cable 141. The connector box 136 also is connected to two lamps 142 and 144 by electric wires 146 and 148 respectively.

The housing 122 includes a lever 152 in the shape of a turtle's head which can be rotated as indicated by arrow 154 in much the same manner as described with respect to previous embodiments. In the embodiment shown in FIG. 7, the adjustment of the position of the lever 152 will dim or brighten the light intensity of the lamps 142 and/or 144. Mounted on the base 126 of the housing 122, there is a slide switch 158 which can be adjusted to allow the lamps 142 and 144 to dim out over a preset duration of time, such from one hour to fifteen minutes or any amount of time in between.

A plunger 160 is formed in the housing 122 and is attached to the dome cover 124, preferably near the upper portion or acme thereof. The plunger 160 extends downward through the housing 122 and has a lower end 162 which may be in contact with a switching mechanism 164 near the base 126. In the embodiment, the cover 124 is spring mounted so that it can be pushed down a small distance and will then return to its original or standing position. As the cover 124 is pushed down, the lower end 162 of the plunger 160 activates the switching mechanism 164. The switching mechanism 164, which is connected to the control unit 134, may have a number of different effects when the cover 126 is pushed downward. For example, a first press down will turn on the lamps 142 and 144. A second press down will start the dimming procedure and may brighten the nightlight bulb 132 as an indication that the count down has commenced. A third press down may turn off the lamps 142 and 144, which would, of course, be unnecessary if they have already dimmed to the extent that they are off.

It will be appreciated that the particular shape and dimensions of the nightlight shown in the various embodiments are not limiting to the invention. Indeed, the nightlight may be in any convenient shape of form, and may be shaped like other animals, structures, dolls or the like. The switches may be differently formed and located, and the intensity adjusters may not be in the form of a sliding switch, but may be in the form of a rotatable knob, rheostat switch, or the like. The time display may be in the form of a LED or LCD mechanism, and, as described with reference to the drawings, multiple lamps may be controlled by the control unit.

The invention is not limited to the precise details described herein. Many types of variations and different embodiments within the scope of the invention may thus be provided. There is no limit as to how the various intensities of the light, fade-out times, or time settings may be made, and any way of carrying out these functions would fall within the scope of the invention.

What is claimed is:

1. A nightlight and control unit comprising:
   a nightlight housing including an illumination member;
   a control unit associated with the nightlight housing for regulating light in a light device connectable to the control unit; and
   input means for programming the control unit.

2. A nightlight and control unit as claimed in claim 1 wherein the housing comprises a dome shaped cover mounted on a flat base, the base having legs, the dome shaped cover and base defining a chamber in which the illumination member is accommodated.

3. A nightlight and control unit as claimed in claim 2 wherein the dome shaped cover is comprised of a fully or partially translucent material to permit light from the illumination member therein to be transmitted through the dome cover.

4. A nightlight and control unit as claimed in claim 3 wherein the housing is configured in the shape selected from the group consisting of a turtle, a toy animal, a toy structure.

5. A nightlight and control unit as claimed in claim 1 wherein the control unit is located within the housing.

6. A nightlight and control unit as claimed in claim 1 wherein the control unit is outside of the housing and electrically connected thereto.

7. A nightlight and control unit as claimed in claim 6 wherein the control unit comprises a box containing circuitry for regulating light in the light device, a light device connector means for electrically connecting the light device with the control unit, a nightlight connecting means for connecting the control unit with the nightlight, and a power cable for connecting the control unit to a power source.

8. A nightlight and control unit as claimed in claim 1 wherein the input means is located on the nightlight housing.

9. A nightlight and control unit as claimed in claim 1 wherein the input means comprises time-setting means, whereby the control unit is programmed to regulate the light device so that the light therefrom fades to off over a preselected time period.

10. A nightlight and control unit as claimed in claim 9 wherein the time-setting means comprises a plurality of buttons on the surface of the housing, each button representing a time period over which the light from the light device is regulated to fade to off.

11. A nightlight and control unit as claimed in claim 10 comprising four buttons, each button regulating the light device to fade over a different time period.

12. A nightlight and control unit as claimed in claim 11 wherein the four buttons comprise a first button representing 15 minutes, a second button representing 30 minutes, a third button representing 45 minutes, and a fourth button representing 60 minutes, for regulating the light device to fade to off.

13. A nightlight and control unit as claimed in claim 9 wherein the time-setting means comprises an annular, rotatable ring member formed on the housing, the annular rotatable ring member being slidable between a first position wherein the light on the light device is regulated to fade over a shorter period of time, and a second position wherein light from the light device is regulated to fade over a longer period of time.

14. A nightlight and control unit as claimed in claim 9 wherein the time-setting means comprises a rotatable knob formed on the housing.

15. A nightlight and control unit as claimed in claim 9 further comprising an adjustment means for setting the initial light intensity of the light device prior to initiation of the fading out process.

16. A nightlight and control unit as claimed in claim 1 further comprising a timer display for indicating time remaining for regulating the light in the light device.

17. A nightlight and control unit as claimed in claim 16 wherein the timer display is comprised of a LED.

18. A nightlight and control unit as claimed in claim 16 wherein the timer display is comprised of a LCD.

19. A nightlight and control unit as claimed in claim 1 further comprising an on/off switch for the illumination member.

20. A nightlight and control unit as claimed in claim 19 wherein the on/off switch is electronically operated by an ambient light detector so that the illumination member will become illuminated when ambient light conditions drop below a preset level.

21. A nightlight and control unit as claimed in claim 1 wherein the illumination member is an incandescent bulb.

22. A nightlight and control unit as claimed in claim 1 wherein the illumination member is at least one light emitting diode (LED).

23. A nightlight and control unit as claimed in claim 1 further comprising adjustment means for adjusting the intensity of the illumination member.

24. A nightlight and control unit as claimed in claim 1 wherein the control unit regulates light from a plurality of light devices.

25. A nightlight and control unit as claimed in claim 24 wherein the control unit can regulate light in the plurality of light devices so as to fade to off over a different period of time for each light device.

26. A nightlight and control unit as claimed in claim 25 further comprising a selector switch for selecting separately each one of the plurality of light devices for programming.

27. A nightlight and control unit as claimed in claim 1 wherein the housing includes a translucent window through which light from the illumination member can pass.

28. A nightlight and control unit as claimed in claim 27 wherein the window is formed in a base portion of the housing.

29. A nightlight and control unit as claimed in claim 1 wherein the input means comprises a remote control transmitter unit, the control unit having receiving means for receiving signals from the remote control transmitter unit for programming the control unit.

30. A nightlight and control unit as claimed in claim 1 wherein the input means further comprises a remote control transmitter unit, the control unit having receiving means for receiving signals from the remote control transmitter unit for programming the control unit.

31. A nightlight and control unit as claimed in claim 1 wherein:
   the housing comprises a dome shaped cover spring mounted on a base member,
   a plunger is formed inside the dome shaped cover, a switch mechanism connects to the control unit, the switch mechanism being activated by the plunger when the dome shaped cover is pushed against the bias of the spring mounting, a first push of the plunger causing the light device to switch on and a second push of the plunger causing the predetermined dimming sequence to begin.

32. A nightlight and control unit as claimed in claim 31 wherein a third push of the plunger causes the light.

33. A nightlight and control unit comprising:
a nightlight housing including an illumination member;
a control unit associated with the nightlight housing for regulating light in a light device other than the illumination member, the light device being connectable to the control unit; and
input for programming the control unit.

* * * * *